United States Patent
Gilbert et al.

(10) Patent No.: US 9,687,048 B2
(45) Date of Patent: Jun. 27, 2017

(54) METHOD OF MAKING A MECHANICAL FASTENER USING A CROWNED SURFACE

(71) Applicant: 3M INNOVATIVE PROPERTIES COMPANY, St. Paul, MN (US)

(72) Inventors: Thomas J. Gilbert, St. Paul, MN (US); Leigh E. Wood, Woodbury, MN (US); Mark A. Peltier, Forest Lake, MN (US); Pieter J. Gagnon, Minneapolis, MN (US)

(73) Assignee: 3M Innovative Properties Company, St. Paul, MN (US)

( * ) Notice: Subject to any disclaimer, the term of this patent is extended or adjusted under 35 U.S.C. 154(b) by 52 days.

(21) Appl. No.: 14/401,326

(22) PCT Filed: Mar. 14, 2013

(86) PCT No.: PCT/US2013/031514
§ 371 (c)(1),
(2) Date: Nov. 14, 2014

(87) PCT Pub. No.: WO2013/172960
PCT Pub. Date: Nov. 21, 2013

(65) Prior Publication Data
US 2015/0096660 A1  Apr. 9, 2015

Related U.S. Application Data

(60) Provisional application No. 61/647,862, filed on May 16, 2012.

(51) Int. Cl.
*A61F 13/62* (2006.01)
*B32B 38/00* (2006.01)
(Continued)

(52) U.S. Cl.
CPC ...... *A44B 18/0011* (2013.01); *A44B 18/0019* (2013.01); *A44B 18/0069* (2013.01);
(Continued)

(58) Field of Classification Search
CPC ......... B32B 2038/0028; B32B 2555/02; A61F 13/622; A61F 13/625; A61F 13/627; B29C 55/08
See application file for complete search history.

(56) References Cited

U.S. PATENT DOCUMENTS 3,252,181 A    5/1966  Hureau
3,616,154 A    10/1971 Dow et al.
(Continued)

FOREIGN PATENT DOCUMENTS

EP    0191355    8/1986
EP    0755665    1/1997
(Continued)

OTHER PUBLICATIONS

Supplementary European Search Report for Application No. EP 13790632, dated Oct. 12, 2015, one page.
(Continued)

*Primary Examiner* — Carson Gross

(57) ABSTRACT

A method of making a mechanical fastener. The method includes providing a slit web having mechanical fastening elements, applying tension to the slit web in the machine direction, and spreading the slit web in the cross-machine direction by moving the slit web over a crowned surface to provide a spread mechanical fastening web. The slit web includes a plurality of interrupted slits that are interrupted by intact bridging regions of the web. The crowned surface may be an air bearing, or at least a portion of the crowned surface is a low-friction surface, and the crowned surface and the slit web are not moving at the same speed in the same direction.

(Continued)

The crowned surface may be provided with at least one ridge.

20 Claims, 7 Drawing Sheets

(51) Int. Cl.
| | | |
|---|---|---|
| *A44B 18/00* | (2006.01) | |
| *A44B 99/00* | (2010.01) | |
| *B32B 37/18* | (2006.01) | |
| *A61F 13/15* | (2006.01) | |
| *B29C 55/08* | (2006.01) | |

(52) U.S. Cl.
CPC ........ *A44B 99/00* (2013.01); *A61F 13/15577* (2013.01); *A61F 13/15764* (2013.01); *A61F 13/622* (2013.01); *B32B 37/18* (2013.01); *B32B 38/0012* (2013.01); *B29C 55/08* (2013.01); *B32B 2038/0028* (2013.01); *B32B 2555/02* (2013.01); *Y10T 156/10* (2015.01)

(56) References Cited

U.S. PATENT DOCUMENTS

| | | | |
|---|---|---|---|
| 3,645,433 A | | 2/1972 | Lucas et al. |
| 3,724,737 A | | 4/1973 | Bodnar |
| 3,985,599 A | | 10/1976 | Lepoutre et al. |
| 3,985,600 A | | 10/1976 | Blais |
| 4,001,366 A | | 1/1977 | Brumlik |
| 4,152,479 A | | 5/1979 | Larsen |
| 4,176,775 A | * | 12/1979 | Brendemuehl .... B65H 23/0258 226/196.1 |
| 4,239,141 A | | 12/1980 | Frye |
| 4,288,884 A | | 9/1981 | Bahls |
| 4,294,240 A | | 10/1981 | Thill |
| 4,560,372 A | | 12/1985 | Pieniak |
| 4,676,784 A | | 6/1987 | Erdman |
| 4,775,310 A | | 10/1988 | Fischer |
| 4,842,794 A | | 6/1989 | Hovis et al. |
| 4,862,565 A | | 9/1989 | Damour |
| 4,925,080 A | | 5/1990 | Crouse et al. |
| 4,969,970 A | | 11/1990 | Suzuki |
| 5,043,036 A | | 8/1991 | Swenson |
| 5,077,870 A | | 1/1992 | Melbye et al. |
| 5,207,962 A | | 5/1993 | Hovis et al. |
| 5,232,533 A | | 8/1993 | Tani et al. |
| 5,256,231 A | | 10/1993 | Gorman et al. |
| 5,260,015 A | | 11/1993 | Kennedy |
| 5,290,377 A | | 3/1994 | Aihara et al. |
| 5,308,345 A | | 5/1994 | Herrin |
| 5,397,316 A | | 3/1995 | LaVon |
| 5,419,695 A | | 5/1995 | Clegg |
| 5,461,760 A | | 10/1995 | Damour |
| 5,476,437 A | | 12/1995 | Damour |
| 5,517,737 A | | 5/1996 | Viltro et al. |
| 5,560,793 A | | 10/1996 | Ruscher et al. |
| 5,605,729 A | | 2/1997 | Mody et al. |
| 5,611,790 A | | 3/1997 | Osborn, III |
| 5,628,097 A | | 5/1997 | Benson et al. |
| 5,660,666 A | | 8/1997 | Dilnik |
| 5,692,271 A | | 12/1997 | Provost |
| 5,713,881 A | | 2/1998 | Rezai |
| 5,729,878 A | * | 3/1998 | Kurihara ............ B65H 23/0258 26/101 |
| 5,776,343 A | | 7/1998 | Cullen et al. |
| 5,791,030 A | | 8/1998 | Aihara et al. |
| 5,891,549 A | | 4/1999 | Beretta |
| 5,953,797 A | | 9/1999 | Provost et al. |
| 6,093,870 A | | 7/2000 | Carlsson |
| 6,132,660 A | | 10/2000 | Kampfer |
| 6,146,369 A | | 11/2000 | Hartman |
| 6,190,594 B1 | | 2/2001 | Gorman et al. |
| 6,262,331 B1 | | 7/2001 | Nakahata |
| 6,287,665 B1 | | 9/2001 | Hammer |
| 6,391,420 B1 | | 5/2002 | Cederblad |
| 6,419,667 B1 | | 7/2002 | Avalon |
| 6,481,063 B2 | | 11/2002 | Shepard |
| 6,489,003 B1 | | 12/2002 | Levitt |
| 6,531,207 B1 | | 3/2003 | Eaton |
| 6,554,754 B2 | | 4/2003 | VanRens |
| 6,582,642 B1 | | 6/2003 | Buzzell |
| 6,627,133 B1 | | 9/2003 | Tuma |
| 6,637,128 B2 | | 10/2003 | Kuroiwa et al. |
| 6,835,256 B2 | | 12/2004 | Menzies |
| 6,843,762 B2 | | 1/2005 | Munche et al. |
| 6,973,702 B2 | | 12/2005 | Harashige |
| 6,984,412 B2 | | 1/2006 | Tanaka |
| 7,001,475 B2 | | 2/2006 | Ausen |
| 7,014,906 B2 | | 3/2006 | Tuman |
| 7,048,818 B2 | | 5/2006 | Krantz |
| 7,048,984 B2 | | 5/2006 | Seth |
| 7,125,400 B2 | | 10/2006 | Igaue |
| 7,198,743 B2 | | 4/2007 | Tuma |
| 7,214,334 B2 | | 5/2007 | Jens et al. |
| 7,219,403 B2 | | 5/2007 | Miyamoto |
| 7,223,314 B2 | | 5/2007 | Provost |
| 7,241,483 B2 | | 7/2007 | Ausen |
| 7,371,302 B2 | | 5/2008 | Miyamoto |
| 7,407,496 B2 | | 8/2008 | Petersen |
| 7,622,180 B2 | | 11/2009 | Seth |
| 7,695,799 B2 | | 4/2010 | Cree |
| 7,855,316 B2 | | 12/2010 | Meyer et al. |
| 7,897,078 B2 | | 3/2011 | Petersen |
| 8,020,262 B2 | | 9/2011 | Oertel |
| 8,889,243 B2 | | 11/2014 | Hanschen |
| 9,138,031 B2 | | 9/2015 | Wood |
| 9,138,957 B2 | | 9/2015 | Wood |
| 9,155,669 B2 | | 10/2015 | Petersen |
| 9,314,962 B2 | | 4/2016 | Rothwell |
| 2002/0086151 A1 | * | 7/2002 | Kiyohara ................ B29C 55/08 428/319.3 |
| 2002/0112325 A1 | | 8/2002 | Keohan |
| 2003/0008106 A1 | | 1/2003 | Guenther |
| 2003/0130644 A1 | | 7/2003 | Baker |
| 2003/0229326 A1 | | 12/2003 | Hovis et al. |
| 2004/0000041 A1 | | 1/2004 | Harashige |
| 2004/0147890 A1 | | 7/2004 | Nakahata et al. |
| 2004/0209042 A1 | | 10/2004 | Peacock |
| 2004/0261230 A1 | | 12/2004 | Neeb |
| 2004/0261232 A1 | | 12/2004 | Kurtz, Jr. |
| 2005/0123720 A1 | | 6/2005 | Suzuki et al. |
| 2006/0288547 A1 | | 12/2006 | Jackson |
| 2007/0107571 A1 | | 5/2007 | Saeki |
| 2007/0131809 A1 | | 6/2007 | Kawashita et al. |
| 2007/0134489 A1 | | 6/2007 | Neugebauer |
| 2008/0201919 A1 | | 8/2008 | Horn |
| 2008/0301912 A1 | | 12/2008 | Maley |
| 2009/0047855 A1 | | 2/2009 | Seth et al. |
| 2009/0311465 A1 | | 12/2009 | De Jong |
| 2010/0100022 A1 | | 4/2010 | Greener |
| 2010/0179463 A1 | | 7/2010 | Greener |
| 2011/0147475 A1 | | 6/2011 | Biegler et al. |
| 2011/0151171 A1 | | 6/2011 | Biegler et al. |
| 2012/0011685 A1 | | 1/2012 | Rocha |
| 2012/0086145 A1 | | 4/2012 | Nakamura |
| 2012/0204383 A1 | * | 8/2012 | Wood ................ A44B 18/0046 24/306 |
| 2012/0330266 A1 | | 12/2012 | Zonneveld et al. |
| 2014/0142533 A1 | | 5/2014 | Peltier |
| 2014/0220328 A1 | | 8/2014 | Ausen |
| 2014/0234606 A1 | | 8/2014 | Ausen |
| 2014/0332999 A1 | | 11/2014 | Rothwell |
| 2014/0349062 A1 | | 11/2014 | Chandrasekaran |
| 2014/0349079 A1 | | 11/2014 | Chandrasekaran |
| 2015/0079337 A1 | | 3/2015 | Ausen |
| 2015/0096659 A1 | | 4/2015 | Gilbert |

FOREIGN PATENT DOCUMENTS

| | | |
|---|---|---|
| EP | 1215036 | 6/2002 |
| EP | 0688665 | 10/2006 |
| EP | 2140775 | 1/2010 |

(56) References Cited

FOREIGN PATENT DOCUMENTS

| | | |
|---|---|---|
| EP | 2277682 | 1/2011 |
| GB | 821959 | 10/1959 |
| GB | 914489 | 1/1960 |
| GB | 1055963 | 1/1967 |
| GB | 1075487 | 7/1967 |
| GB | 1275541 | 5/1972 |
| GB | 2017485 | 10/1979 |
| JP | 36-16493 | 9/1961 |
| JP | 39-22059 | 10/1964 |
| JP | 2010-29532 | 2/2010 |
| WO | WO 9402091 | 2/1994 |
| WO | WO 9610481 | 4/1996 |
| WO | WO 2004-091437 | 10/2004 |
| WO | WO 2005-122818 | 12/2005 |
| WO | WO 2011-163020 | 12/2011 |
| WO | WO 2012-112768 | 8/2012 |
| WO | 2013-032683 | 3/2013 |
| WO | WO 2013-052371 | 4/2013 |
| WO | WO 2013-170480 | 11/2013 |
| WO | WO 2014-164242 | 10/2014 |

OTHER PUBLICATIONS

US 5389416, 02/1995, Mody et al. (withdrawn).
International Search Report for PCT International Application No. PCT/US2013/031514, mailed on Jun. 26, 2013, 3pgs.

* cited by examiner

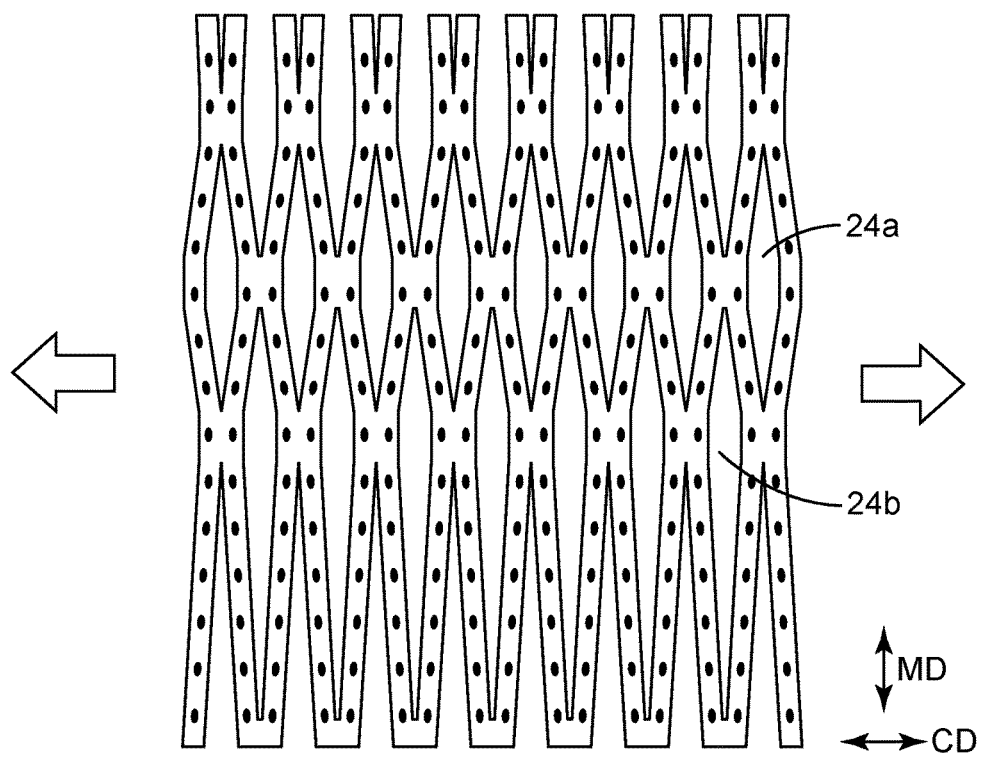
FIG. 3B
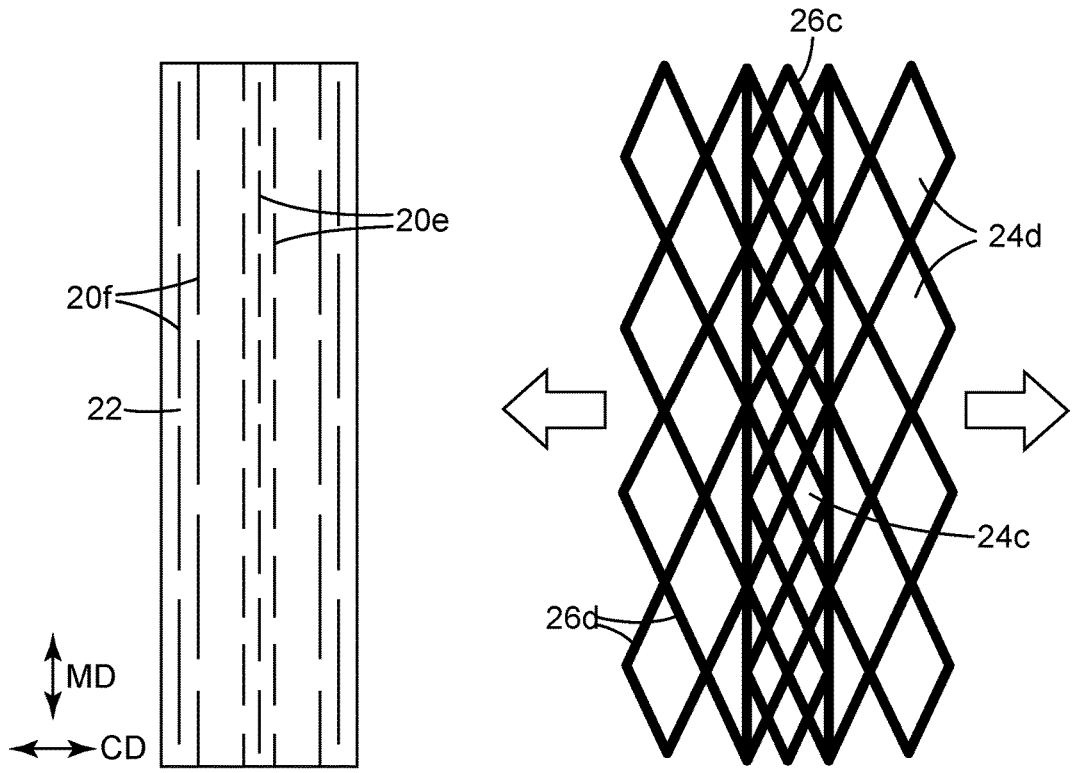
FIG. 4A
FIG. 4B

METHOD OF MAKING A MECHANICAL FASTENER USING A CROWNED SURFACE

CROSS REFERENCE TO RELATED APPLICATIONS

This application is a national stage filing under 35 U.S.C. 371 of PCT/US2013/031514, filed Mar. 14, 2013, which claims priority to U.S. Application No. 61/647,862, filed May 16, 2012, the disclosure of which is incorporated by reference in its entirety herein.

BACKGROUND

Hook and loop fastening systems, where the hook member typically includes a plurality of closely spaced upstanding projections with loop-engaging heads, and the loop member typically includes a plurality of woven, nonwoven, or knitted loops, are useful for providing releasable attachment in numerous applications. For example, hook and loop fastening systems are widely used in wearable disposable absorbent articles to fasten such articles around the body of a person. In typical configurations, a hook strip or patch on a fastening tab attached to the rear waist portion of a diaper or incontinence garment, for example, can fasten to a landing zone of loop material on the front waist region, or the hook strip or patch can fasten to the backsheet (e.g., nonwoven backsheet) of the diaper or incontinence garment in the front waist region. Hook and loop fasteners are also useful for disposable articles such as sanitary napkins. A sanitary napkin typically includes a back sheet that is intended to be placed adjacent to the wearer's undergarment. The back sheet may comprise hook fastener elements to securely attach the sanitary napkin to the undergarment, which mechanically engages with the hook fastener elements.

Some hook members have been made with openings in the backing from which the hooks project. See, e.g., U.S. Pat. No. 4,001,366 (Brumlik) and U.S. Pat. No. 7,407,496 (Peterson) and Int. Pat. Appl. Pub. Nos. WO 2005/122818 (Ausen et al.) and WO 1994/02091 (Hamilton).

Some nonwoven materials have been made with openings. Such nonwovens have been attached to elastics or extensible pleated backings. See, e.g., U. S. Pat. Appl. Pub. No. 2004/0147890 (Nakahata et al.), Int. Pat. Appl. Pub. No. WO 1996/10481 (Abuto et al.), and European Patent No. EP 1066008 B1 (Eaton et al.).

SUMMARY

The present disclosure provides a method of making mechanical fastener using a web process. The mechanical fastener comprises openings made from multiple strands of a slit web having mechanical fastening elements with the strands attached to each other at bridging regions of the web and separated from each other between at least some of the bridging regions. The method includes spreading the slit web in the cross-machine direction by moving the slit web over a crowned surface.

In one aspect, the present disclosure provides a method of making a mechanical fastener. The method includes providing a slit web having mechanical fastening elements, applying tension to the slit web in the machine direction, and spreading the slit web in the cross-machine direction by moving the slit web over a crowned surface to provide a spread mechanical fastening web. The slit web includes a plurality of laterally separated interrupted slits that are interrupted by intact bridging regions of the web. The interrupted slits extend in a first direction not parallel to a cross-machine direction. For at least some adjacent interrupted slits, the intact bridging regions are staggered in a direction transverse to the first direction. The spread mechanical fastening web includes multiple strands of the slit web attached to each other at least at some of the intact bridging regions and separated from each other between at least some of the intact bridging regions. At least one of the following is true about the crowned surface: at least a portion of the crowned surface is an air bearing or the crowned surface and the slit web are not moving at the same speed in the same direction. In the latter case, at least a portion of the crowned surface is a low-friction surface. In some embodiments, the crowned surface does not rotate. In some embodiments, the crowned surface is provided with at least one ridge.

The method according to any of the above aspects allows openings to be provided in the mechanical fastener without wasteful material loss. The degree of spreading of the strands in the methods disclosed herein may be adjusted based upon, for example, the desired appearance, weight, or cost in the final product.

The method disclosed herein may be useful, for example, for making a reticulated mechanical fastening web, laminate, strip, or patch that has a unique and attractive appearance. The openings can provide breathability and flexibility to the mechanical fastener, which may enhance the comfort of the wearer, for example, of an absorbent article comprising the mechanical fastener made by the method disclosed herein. The mechanical fastener also is typically able to cover a relatively large area with a relatively small amount of material, which may lower its cost. Also, because of the large area that may be covered by the mechanical fastener in an absorbent article, the mechanical fastener may provide performance enhancement, for example, by resist shifting forces such as torsional or rotational forces caused by movement of the wearer of the absorbent article. For example, in use, fitting an absorbent article such as a diaper about the wearer usually requires the front and back waist portions of the diaper to overlap each other. As the diaper is worn the movements of the wearer tend to cause the overlapping front and back waist portions to shift position relative to each other. Unless such shifting is limited, the fit and containment characteristics of the diaper may be degraded as the diaper is worn. The mechanical fastener made according to the present disclosure may provide improved fit and closure stability by resisting such shifting because of its relatively larger area and flexibility.

In this application, terms such as "a", "an" and "the" are not intended to refer to only a singular entity, but include the general class of which a specific example may be used for illustration. The terms "a", "an", and "the" are used interchangeably with the term "at least one". The phrases "at least one of" and "comprises at least one of" followed by a list refers to any one of the items in the list and any combination of two or more items in the list. All numerical ranges are inclusive of their endpoints and non-integral values between the endpoints unless otherwise stated.

The term "low-friction surface" refers to a surface made from any material or coated with any material that allows slit web to slip over the crown surface to at least some degree. The "low-friction surface" typically has a low coefficient of friction relative to the slit web. The coefficient of friction between the "low-friction surface" and the slit web is typically up to 0.2. In some embodiments, "low-friction surface" can mean non-rubber surface.

The terms "first" and "second" are used in this disclosure. It will be understood that, unless otherwise noted, those terms are used in their relative sense only. For these components, the designation of "first" and "second" may be applied to the components merely as a matter of convenience in the description of one or more of the embodiments.

The terms "multiple" and "a plurality" refer to more than one.

The term "opening" should be understood to be a void space in the mechanical fastener material that is surrounded by the mechanical fastener web. One opening is typically enclosed by two of the multiple strands.

The term "web" can refer to a continuous or running web, sometimes having an indefinite length. A web can typically be handled in a roll-to-roll process. The term "machine direction" (MD) as used above and below denotes the direction of a running web of material during the manufacturing of the mechanical fastener. When a mechanical fastening strip is cut from a continuous web, the machine direction corresponds to the length "L" of the mechanical fastening strip. As used herein, the terms "machine direction" and "longitudinal direction" are typically used interchangeably. The term "cross-machine direction" (CD) as used above and below denotes the direction which is essentially perpendicular to the machine direction. When a mechanical fastening strip is cut from a continuous web, the cross-machine direction corresponds to the width "W" of the mechanical fastening strip.

The above summary of the present disclosure is not intended to describe each disclosed embodiment or every implementation of the present disclosure. The description that follows more particularly exemplifies illustrative embodiments. It is to be understood, therefore, that the drawings and following description are for illustration purposes only and should not be read in a manner that would unduly limit the scope of this disclosure.

BRIEF DESCRIPTION OF THE DRAWINGS

The disclosure may be more completely understood in consideration of the following detailed description of various embodiments of the disclosure in connection with the accompanying drawings, in which:

FIG. 3B is a top view of a portion of the slit web similar to FIG. 3A after it is spread according to the method disclosed herein;

FIG. 4A is a schematic top view of another embodiment of a portion of a slit web useful for the methods of making a mechanical fastener disclosed herein;

FIG. 4B is a schematic top view of the portion of the slit web of FIG. 4A after it is spread according to the method disclosed herein;

DETAILED DESCRIPTION

Figure 1A:
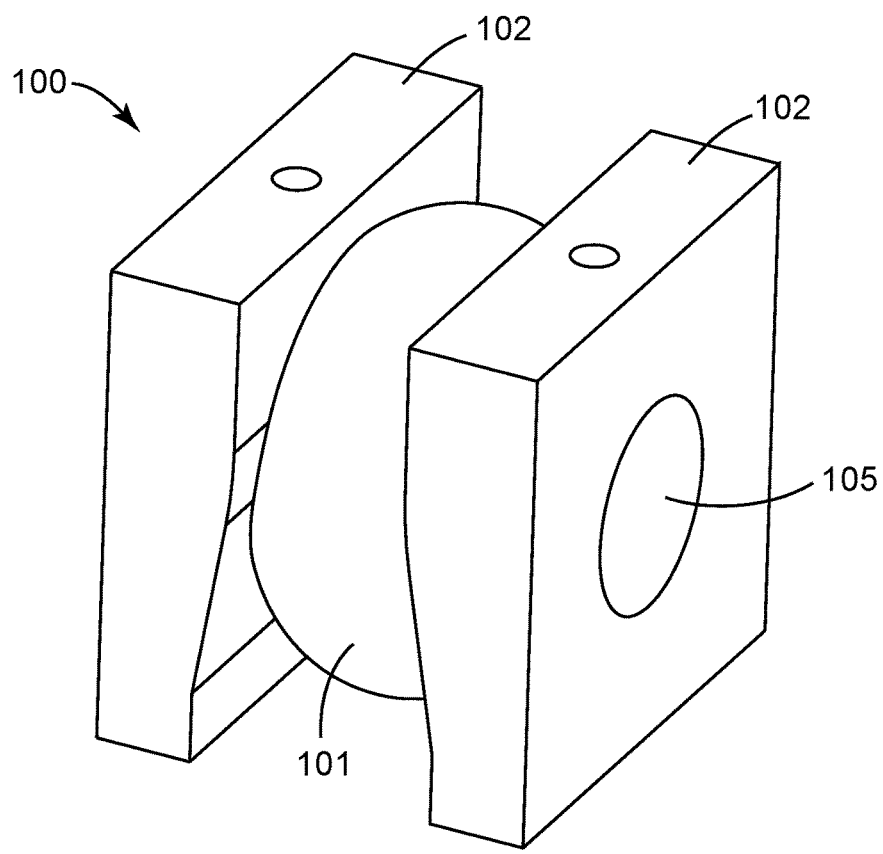
FIG. 1A is a perspective view of one embodiment of a crowned surface between mounting structures useful for carrying out the method according to the present disclosure.

Reference will now be made in detail to embodiments of the disclosure, one or more examples of which are illustrated in the drawings. Features illustrated or described as part of one embodiment can be used with other embodiments to yield still a third embodiment. It is intended that the present disclosure include these and other modifications and variations.

In this application, a crowned surface can be considered any forming surface that lengthens the path of a portion of the slit web. A crowned surface useful for practicing the present disclosure has a varying height dimension in a direction corresponding to the CD of the slit web. Generally, the height of the crowned surface is greatest at its center. The crowned surface may be a smooth surface having a generally spherical or elliptical shape in which the diameter or axis continuously increases toward its center. However, a crowned surface useful for practicing the present disclosure need not have a uniform height variation over its entire portion that contacts the slit web. For example, the crown surface may have a flat portion where the slit web first contacts it, and the curvature of the crowned surface in a direction corresponding to the CD of the slit web may increase in the direction of the slit web path. The crowned surface may also have, in some embodiments, ridges or other surface irregularities.

Any surface over which a web in tension is bent or wrapped around is believed to impart a force on the web that is normal or perpendicular to the web. Because of the varying height of a crowned surface, the force imparted on a web by a crowned surface is not evenly distributed. Without wanting to be bound by theory, it is believed that the crowned surface can spread open a slit web as described herein because a component of the normal force generated by a crowned surface will be in the cross-web direction. The cross-direction strength of the web is relatively low because of the slits in the web, and the amount of tension in the web that would resist spreading is low. Therefore, the cross-directional component of the force generated by a crowned surface can induce spreading of a slit web.

The amount of spreading that can result by moving a slit web over a crowned surface can be limited by the frictional force resisting the cross-directional movement of the spreading web. Because of this, it may be desirable to minimize the friction between the slit web and the crowned surface. Such friction can be decreased if at least a portion of the crowned surface is a low-friction surface. For example, a least a portion of the crowned surface can be made from a low-friction material or can be coated with a low-friction coating. Also, if the crowned surface is an air bearing, friction between the slit web and the crowned surface may be decreased. Since the coefficient of kinetic friction of two materials is generally lower than the corresponding coefficient of static friction, it is typically desirable that the crowned surface and the slit web are not moving at the same speed in the same direction so that the crowned surface and the slit web can have a "slipping" interface. Accordingly, in some embodiments, the crowned surface does not rotate, or, in other words, it is stationary. In other embodiments, the crowned surface may be rotating in a direction opposite to the direction of the slit web or can be rotating at a different speed than the slit web in the machine direction.

FIG. 1A illustrates an embodiment of an apparatus 100 useful for the method of making a mechanical fastener disclosed herein. Apparatus 100 includes a crowned surface 101 and mounting structures 102 useful for mounting the crowned surface in a roll-to-roll assembly through shaft openings 105. In the embodiment illustrated in FIG. 1A, the mounting structures 102 are useful for mounting the crowned surface 101 in a stationary or non-rotating fashion. In some embodiments, crowned surface 101 is an air bearing, which is useful, for example, for lowering the friction between the crowned surface 101 and the slit web. In some embodiments, crowned surface 101 can be made from a low-friction material such as smooth or polished metal (e.g., aluminum or steel), smooth plastic (e.g., polytetrafluoroethylene, polyoxymethylene, polyether ether ketone, or other engineering plastics), or a smooth plastic composite material. In some embodiments, crowned surface 101 can be coated with a low-friction coating (e.g., plasma or polytetrafluoroethylene coating).

Figure 1B:
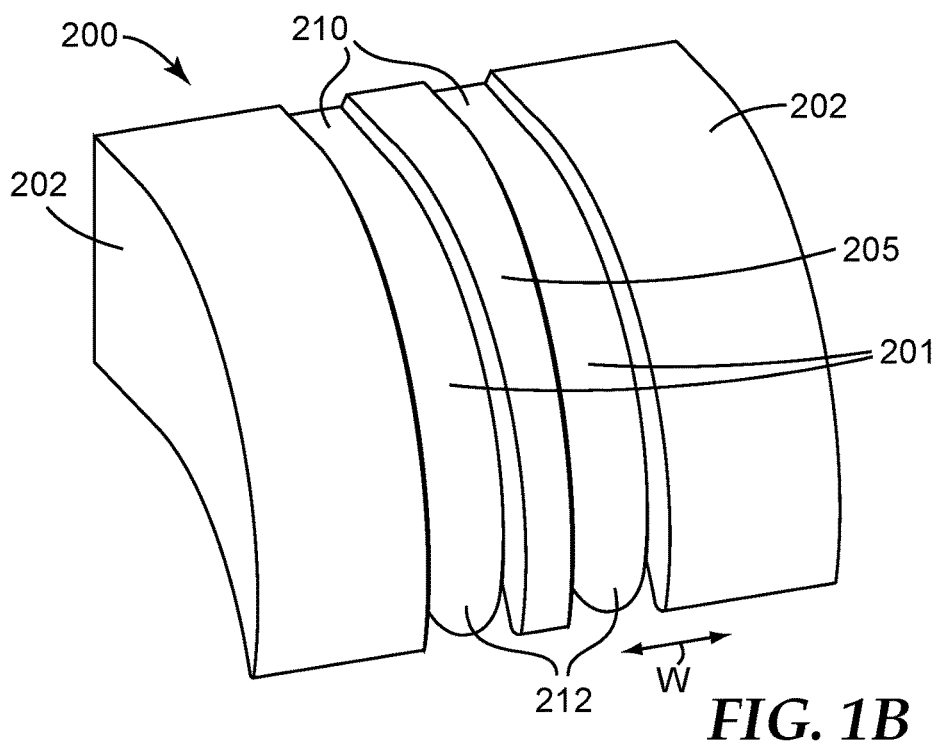
FIG. 1B is a perspective view of another embodiment of two crowned surfaces between mounting structures useful for carrying out the method according to the present disclosure.

FIG. 1B illustrates another embodiment of an apparatus 200 useful for the method of making a mechanical fastener disclosed herein. Apparatus 200 includes two crowned surfaces 201 separated by a separation ridge 205. The two crowned surfaces 201 may be useful for spreading two slit webs at the same time, which can be useful, for example, for simultaneously making fastening tabs for the left and right sides of an absorbent article. Each of crowned surfaces has curvature in the width direction "W" that varies from flat surfaces 210 to locations 212 having more curvature. Flat surfaces 210 can serve as entry points for the two slit webs (not shown), and as the curvature of the crowned surfaces 201 increases in the width direction "W", the component of the normal force in the CD imparted by the crowned surface onto the slit web increases as the slit web moves along the path from flat surfaces 210 to locations 212. Mounting structures 202 can be useful for mounting the apparatus 200 in a stationary configuration. The crowned surfaces 201 can be an air bearing or can be made from any of the low-friction materials or coated with any of the low-friction coatings described above in connection with the embodiment shown in FIG. 1A.

Figure 1C:
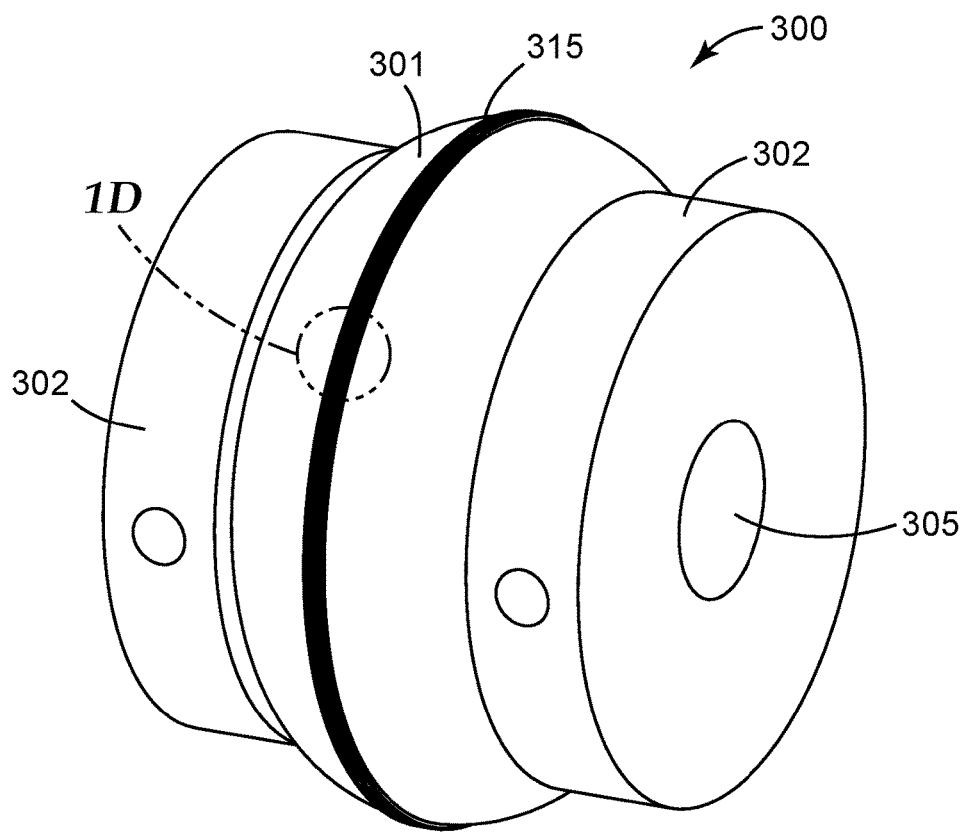
FIG. 1C is a perspective view of yet another embodiment of a crowned surface between mounting structures useful for carrying out the method according to the present disclosure.
Figure 1D:
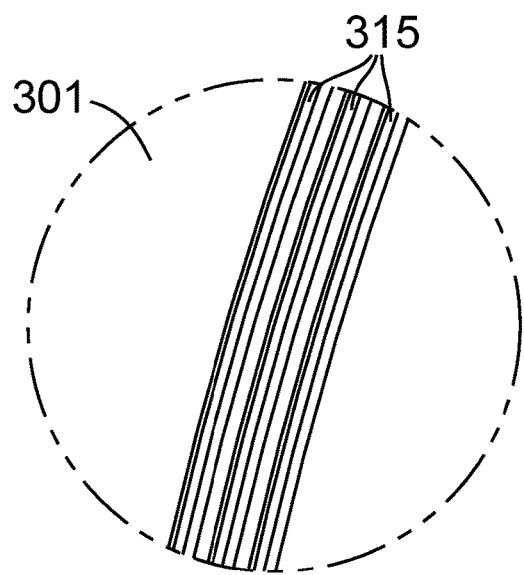
FIG. 1D is an expanded view of the circled area labeled 1D in FIG. 1C.

The cross-directional forces imparted by the crown surface on the slit web can cause the web to slide off of the crowned surface, for example, if the cross-directional force in one direction becomes greater for some reason than the cross direction force in the opposite direction. Therefore, in some embodiments, it is useful to have a guiding mechanism to keep the slit web centered on the crown surface. FIG. 1C illustrates another embodiment of an apparatus 300 useful for the method of making a mechanical fastener disclosed herein. Apparatus 300 includes a crowned surface 301 and mounting structures 302 useful for mounting the crowned surface in a roll-to-roll assembly through shaft openings 305. The illustrated mounting structures 302 can be useful for mounting the crowned surface 301 in a stationary or non-rotating fashion. Crowned surface 301 includes a group of three ridges 315 that may be useful, for example, for guiding the slit web. Ridges 315 are shown more clearly in the expansion shown in FIG. 1D. Although the illustrated embodiment shows three ridges 315, other numbers of ridges may be useful, for example, one or two ridges. The ridges 315 are typically centered on the crowned surface at its apex as shown in FIG. 1C. Ridges 315 may be useful for guiding the slit web in a variety of ways. For example, the mechanical fastening elements on the slit web may be male fastening elements, and the slit web may be arranged so that the male fastening elements face toward the crowned surface 300. Guiding ridges 315 fit between the male fastening elements (e.g., rows of male fastening elements as described further below) to help hold the slit web in place on the crowned surface 300. In another embodiment, the slit web is formed with at least one continuous rib centered on a surface opposite to a surface having the mechanical fastening elements. In this embodiment, the slit web may be arranged so that the continuous rib(s) faces toward the crowned surface 300, and the continuous rib(s) fits between the guiding ridges 315 on the crowned surface 300. Ridges such as 315 may also be useful on the embodiment shown in FIG. 1B.

In some embodiments, at least one ridge provided in the center of the crowned surface (e.g., at its apex) may be made from a high-friction material such as a rubbery material. A narrow ridge of a high-friction material may be useful for keeping the slit web centered on the crowned surface. In some embodiments, the ridge may be made to rotate to increase the coefficient of friction between the slit web and the ridge.

Any of the crowned surfaces 101, 201, and 301 may be useful to spread a slit web in a cross-machine direction to provide openings. Various embodiments of the slit web useful in the method disclosed herein before and after they are spread are illustrated in FIGS. 2A through 2C, 3A, 3B, 4A, and 4B and described below.

Figure 2A:
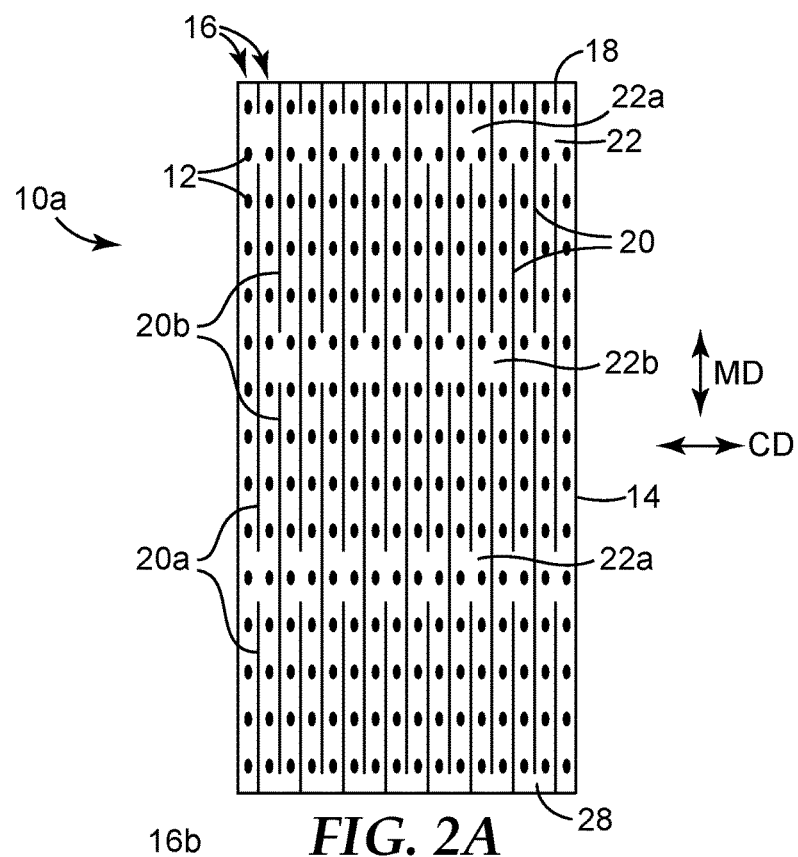
FIG. 2A is a top view of an embodiment of a portion of a slit web useful for the method of making a mechanical fastener disclosed herein.

FIG. 2A illustrates an example of a portion of a slit web 10a with interrupted slits 20 that can be spread using the method disclosed herein. In the illustrated embodiment, the mechanical fastening elements of the slit web 10a are male fastening elements 12. Illustrated slit web 10a has a thermoplastic backing 14 with multiple rows 16 of male fastening elements 12 projecting from a first surface of the backing 14. The first surface of the backing is the surface that is visible in FIG. 2A. The first surface (that is, the surface with mechanical fastening elements) can also be called the first major surface in any of the embodiments disclosed herein. In the illustrated embodiment, the multiple rows 16 of male fastening elements 12 are aligned in the MD although this is not a requirement. The term "row" refers to male fastening elements lined up in a particular direction. The row or line of male fastening elements may be substantially straight.

In the portion of slit web 10a, interrupted slits 20 are cut into the backing between some pairs of adjacent rows 16 of male fastening elements 12. When an interrupted slit is cut between adjacent rows of male fastening elements 12, it typically means that the particular slit does not cross over a row of male fastening elements 12. The illustrated interrupted slits 20 are linear in the same direction as the multiple rows 16, which in the illustrated embodiment is the MD, and extend from the top edge 18 to the bottom edge 28 of the backing 14. The interrupted slits are interrupted by intact bridging regions 22 of the backing 14. The bridging regions 22 are regions where the web is not cut through, and at least a portion of the bridging regions 22 can be considered collinear with interrupted slit 20. The intact bridging regions 22 divide the interrupted slits into a series of spaced apart slit portions 20a. The spaced apart slit portions 20a and 20b and consequently bridging regions 22a and 22b of adjacent interrupted slits are staggered in a direction "CD" perpendicular to the direction "MD" of the interrupted slits 20. The bridging regions are staggered such that bridging region 22b is located substantially midway between bridging regions 22a in the direction "MD". However, in some embodiments, the upstanding posts 12, interrupted slits 20, and bridging regions 22, 22a, and 22b may be positioned in other arrangements. When the slit portions and bridging regions are staggered, the number of bridging regions necessary to make the slit mechanical fastener handle as an integral unit can be minimized.

In some embodiments of the method disclosed herein, the interrupted slits 20 extend in the MD. In some embodiments, the interrupted slits extend in a first direction that is nonparallel to the CD. When it is said that an interrupted slit "extends" in a first direction, it is meant that the slit is arranged or aligned in that direction or at least predominantly in that direction. The slit may be linear. As used herein a "linear" slit can be defined by two points in a line on the web. The slit may also be substantially linear, which means that the slit can have a slight curvature or slight oscillation. Some oscillation or curvature may result, for example, from the process of slitting a continuous web as would be understood by a person skilled in the art. In some embodiments of mechanical fasteners with male fastening elements made according to the method of the present disclosure, any oscillation or curvature is such that the slit generally does not have a portion that crosses over a row of male fastening elements aligned in the first direction. The interrupted slit may also have a wavy or sawtooth pattern with a small amplitude, and such a slit would also be considered to extend in predominantly in a certain direction.

The particular arrangement of the bridging regions 22, 22a, and 22b can be designed, for example, based on the desired length of the slits and the amount of spreading desired for the multiple strands 26. Various lengths of bridging regions 22, 22a, and 22b may be useful. In some embodiments, any bridging regions 22 in a given interrupted slit 20 have a combined length in the direction of the interrupted slit of up to 50 (in some embodiments, 40, 30, 25, 20, 15, or 10) percent of the length of the slit web in the MD. In some embodiments, for maximizing the ability of the slit web 10a to spread, it may be desirable to minimize the combined length of the bridging regions in the direction of the interrupted slit. Minimizing the combined length of the bridging regions 22 in the direction of the interrupted slit may be accomplished by at least one of minimizing the length of any particular bridging region 22 or maximizing the distance between bridging regions 22. In some embodiments, the length of one bridging region in the direction of the interrupted slit is up to 3, 2, or 1.5 mm and at least 0.25, 0.5, or 0.75 mm. In some embodiments, the number of bridging regions along the length of the slit web 10a in the direction of the interrupted slit is up to 1.5, 1.25, 1.0, 0.75, 0.60, or 0.5 per cm. The distance between bridging regions 22 in the direction of the interrupted slit may be, for example, at least 0.75, 1.0, 1.25, 1.5, or 1.75 cm. Furthermore, the length of the interrupted slit portions between bridging regions can be adjusted and may be selected to maximize the distance between bridging regions. In some embodiments, the length of the slit portions 20a, 20b is at least 8 (in some embodiments, at least 10, 12, 14, 15, 16, 17, 18, 19, or 20) mm. Typically, the interrupted slits of the slit webs 10a useful for practicing the present disclosure have longer slit regions and shorter bridging regions than perforations that are designed to allow easy separation of two parts of a film.

In some embodiments, slit portions 20a, 20b have a regular pattern that repeats down the slit web 10a. In some embodiments, spacing (e.g., in the MD or other direction of the interrupted slits) between slit portions 20a may be uniform or substantially uniform (that is, the spacing may differ by up to 2 percent, 1 percent, or less than 1 or 0.5 percent) although this is not a requirement.

For any of the embodiments of the method of making a mechanical fastener disclosed herein, the number of interrupted slits and resulting openings may be adjusted depending on the desired spread mechanical fastening web. The interrupted slits may be evenly spaced or unevenly spaced as desired. In some embodiments, there are up to 10, 9, 8, 7, 6, 5, 4, 3, 2, or 1 interrupted slits per 10 mm across the width of the slit web in the CD. Changing the number of interrupted slits across the slit web may be related to the number of rows of male fastening elements between any two adjacent interrupted slits, depending on the density of the male fastening elements on the backing. The number of rows of male fastening elements between any two adjacent interrupted slits may be adjusted depending on the requirements of the application. In some embodiments, there are up to 10, 9, 8, 7, 6, 5, 4, 3, 2 rows, or 1 row of male fastening elements between any two adjacent interrupted slits. Typically, the width dimension of each of the multiple strands formed between interrupted slits is wider than at least the bases of the upstanding posts of the male fastening elements. In some embodiments, there is an interrupted slit between every row or every other row of male fastening elements. In the illustrated embodiment, the interrupted slits 20 are evenly spaced among the rows of male fastening elements 12 although this is not a requirement. For multiple rows 16 of male fastening elements 12 that are evenly spaced, as illustrated, the spacing (e.g., distance in the CD in the illustrated embodiment) between multiple rows 16 may differ by up to 10, 5, 2.5, or 1 percent. Likewise, for interrupted slits that are evenly spaced, the spacing (e.g., distance in the CD) between the interrupted slits may differ by up to 10, 5, 2.5, or 1 percent.

Figure 2B:
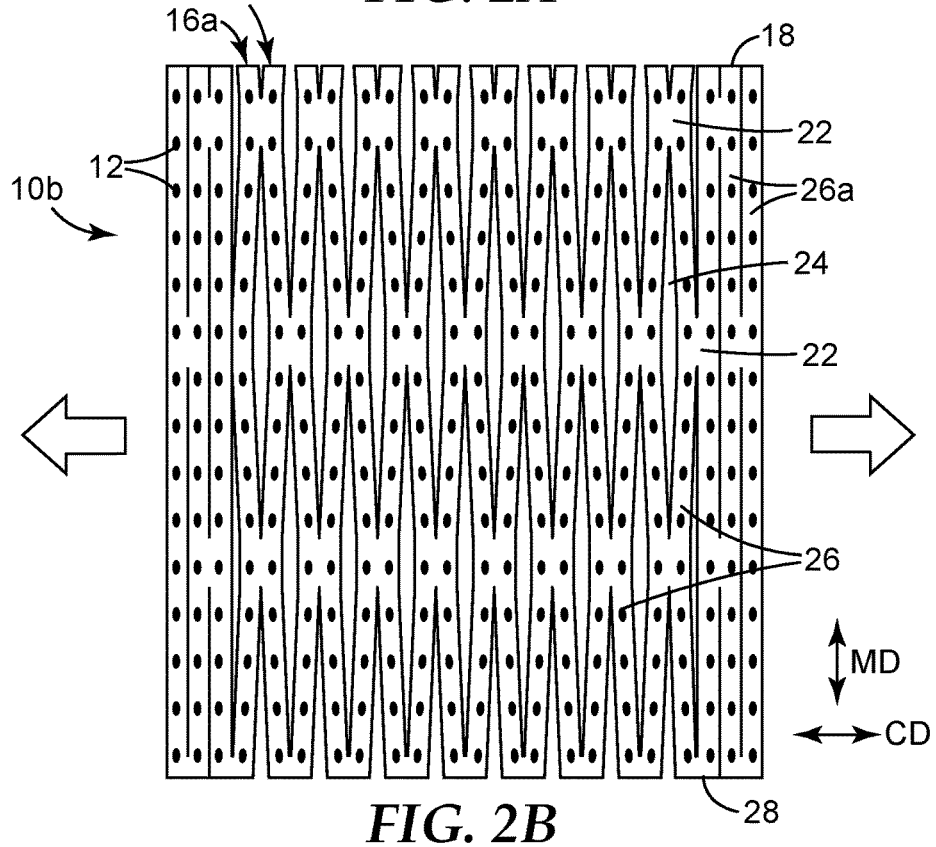
FIG. 2B is a top view of the portion of the slit web similar to FIG. 2A after it is spread according to the method disclosed herein.
Figure 2C:
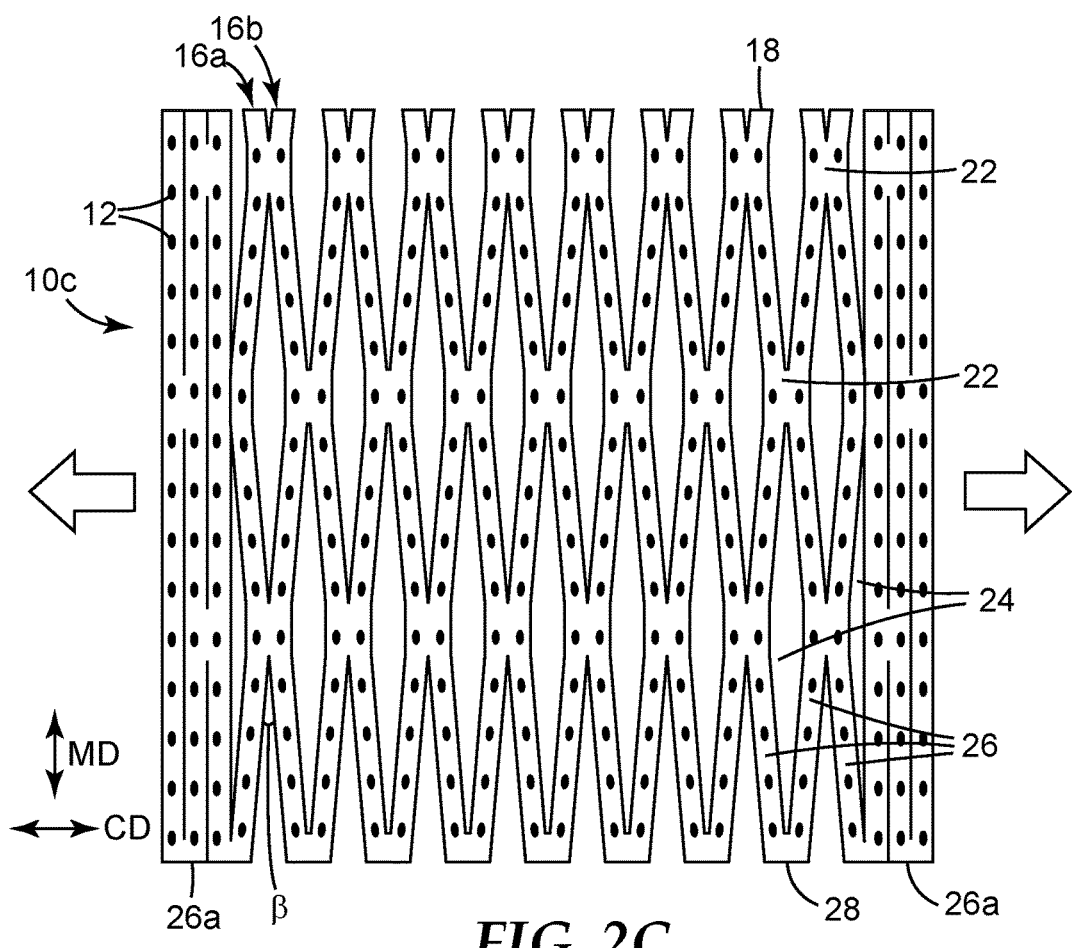
FIG. 2C is a top view of the portion of the slit web of FIG. 2B after it is spread to a greater extent than shown in FIG. 2B.

FIGS. 2B and 2C illustrate the effect of spreading the slit backing like that shown in FIG. 2A to different extents. When the slit backing 10b is spread in the direction of the arrows shown, multiple strands 26 of the backing are provided, and the separation between at least some of the multiple strands creates openings 24. The method according to the present disclosure typically increases the width of the slit web (that is, the dimension in the CD).

FIG. 2C illustrates a greater amount of spreading than FIG. 2B. The amount of spreading provided in the method disclosed herein can be controlled by a variety of factors including the geometry of the crowned surface, the amount of tension in the machine direction, and the coefficient of friction between the slit web and the crowned surface as described above. In some embodiments, spreading the slit web is carried out with multiple crowned surfaces in a series, which can also affect the extent of spreading. In some embodiments, the width of the spread mechanical fastening web is at least 5, 10, 15, 20, or 25 percent greater than the width of the input slit web. In some embodiments, the width of the spread mechanical fastening web is up to 40, 50, 75, 100, 150, or 200 percent greater than the width of the input slit web. If only a single crowned surface is used in the method disclosed herein, the width of the spread mechanical fastening web is typically up to 40, 50, 75, or 100 percent greater than the width of the input slit web.

In the embodiment illustrated in FIG. 2C, at least two strands 26a, including at least two rows of male fastening elements on each edge of the mechanical fastener, are not separated. This may be accomplished by selection of the geometry of the crowned surface and width of the slit web. A spread mechanical fastening web having strands on the edge that are not spread apart may be advantageous in some embodiments, for example, to provide a reticulated mechanical fastening strip or patch with a straight edge.

While FIGS. 2A through 2C illustrate a backing 14 with male fastening elements 12 that comprise upstanding posts, it should be understood that a loop material can be slit to provide slit web 10a and spread while moving over a crowned surface 101, 201, and 301 in the same manner to the same extent as spread mechanical fastening webs 10b and 10c.

Figure 3A:
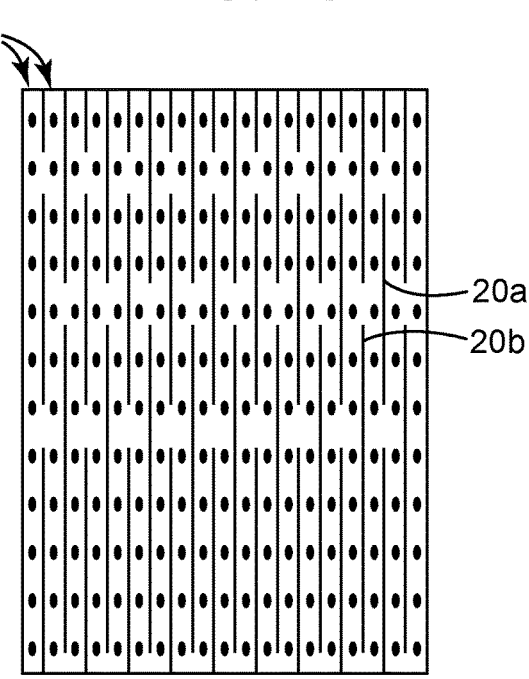
FIG. 3A is a top view of another embodiment of a portion of a slit web useful for the methods of making a mechanical fastener disclosed herein.

FIG. 3A illustrates an example of a slit web portion having male fastening elements, which is similar to the portion of slit web 10a shown in FIG. 2A. However, in the embodiment shown in FIG. 3A, slit portions 20a have different lengths than slit portions 20b of adjacent slits, which results in openings 24a and 24b having different sizes after the slit web is spread as shown in FIG. 3B. That is, openings 24a are shorter in the MD than openings 24b. The slit portions of the smaller size 20a and slit portions of the larger size 20b each may be aligned with each other across the slit web as shown in FIG. 3A. Or in other embodiments, slits of the same size may be offset relative to each other in a regular pattern. Furthermore, referring again to FIG. 2A, the length of the bridging regions 22 may be made to vary within a strand 26 or between strands 26 as desired for a particular application or appearance. Although FIGS. 3A and 3B illustrate mechanical fasteners with male fastening elements, the same slitting pattern and spreading using the method disclosed herein can be carried out with a loop material.

FIG. 4A illustrates an example of a slit web having mechanical fastening elements, which is similar to the slit mechanical fastener 10a shown in FIG. 2A. However, in the embodiment shown in FIG. 4A, slit portions 20e have different lengths than slit portions 20f, which results in openings 24c and 24d having different sizes after the slit web is spread as shown in FIG. 4B. In contrast to the embodiment shown in FIGS. 3A and 3B, which illustrates interrupted slits with slit portions of different lengths in the MD and the corresponding resulting openings, FIGS. 4A and 4B illustrate patterns of slit portions of different lengths in different zones in the CD of the slit web. The multiple strands 26c and 26d have a different appearance from each other in the same spread mechanical fastening web, for example, multiple strands 26c and 26b zig-zag or undulate with a different wavelength and amplitude. The slit web and the spread mechanical fastening web shown in FIGS. 4A and 4B, respectively, may include male or female mechanical fastening elements (not shown).

For any of the embodiments of the method of making a mechanical fastener disclosed herein, the openings formed by the separation of the multiple strands between at least some of the bridging regions are in the form of a repeating pattern of geometric shapes. In the illustrated embodiments, the geometric shapes are polygons, which may be quadrilaterals such as rhombuses. In some embodiments of the spread mechanical fastening web, including the embodiment illustrated in FIG. 2C, the multiple strands of the web attached to each other at least at some of the intact bridging regions form an angle β of less than 90 degrees, in some embodiments, up to 60 degrees, 45 degrees, or 20 degrees, and in some embodiments, in a range from 0.5 to 20 degrees. For example, in some embodiments, when a slit web having 19 mm slit portions 20a is spread so that the width of the spread mechanical fastening web is 100% greater than the input slit web, the angle β is typically in a range from about 5 to 10 degrees. In some embodiments, curved lines may be used, which can result in crescent shaped openings after spreading. As shown in FIG. 4B, there may be more than one repeating pattern of geometric shaped openings. The openings may be evenly spaced or unevenly spaced as desired. For openings that are evenly spaced, the spacing (e.g., distance in the CD) between the openings may differ by up to 10, 5, 2.5, or 1 percent.

Although the methods of making mechanical fastener illustrated in FIGS. 2A through 2C, 3A and 3B, and 4A and 4B each show interrupted slits extending parallel to the MD of the slit web, interrupted slits may be made in any desired direction not parallel to the CD. For example, interrupted slits may be made at an angle from 1 to 85 degrees to the MD of the slit web. In some embodiments, interrupted slits are made at an angle in a range from 35 to 55 degrees (e.g., 45 degrees) to the MD of the slit web.

The method according to the present disclosure may be useful for any width of the slit web in the CD. For example, the slit web may have a width in the CD in a range from 1 cm to 10 cm, 1 cm to 5 cm, or 1 cm to 3 cm wide.

In some embodiments, the slit web useful in the method disclosed herein or the resulting spread mechanical fastening web are made of a thermoplastic material. Suitable thermoplastic materials for mechanical fasteners include polyolefin homopolymers such as polyethylene and polypropylene, copolymers of ethylene, propylene and/or butylene; copolymers containing ethylene such as ethylene vinyl acetate and ethylene acrylic acid; polyesters such as poly(ethylene terephthalate), polyethylene butyrate and polyethylene napthalate; polyamides such as poly(hexamethylene adipamide); polyurethanes; polycarbonates; poly(vinyl alcohol); ketones such as polyetheretherketone; polyphenylene sulfide; and mixtures thereof. Typically, the thermoplastic is a polyolefin (e.g., polyethylene, polypropylene, polybutylene, ethylene copolymers, propylene copolymers, butylene copolymers, and copolymers and blends of these materials).

In the embodiments of the slit web useful in the method disclosed herein or the resulting spread mechanical fastening web that includes male fastening elements, the backing and the male fastening elements are typically integral (that is, formed at the same time as a unit, unitary). Upstanding posts on a backing can be made, for example, by feeding a thermoplastic material onto a continuously moving mold surface with cavities having the inverse shape of the posts. The thermoplastic material can be passed between a nip formed by two rolls or a nip between a die face and roll surface, with at least one of the rolls having the cavities. The cavities may be in the inverse shape of a capped post having a loop-engaging head or may be in the inverse shape of an upstanding post without loop-engaging heads (e.g., a precursor to a male fastening element). Pressure provided by the nip forces the resin into the cavities. In some embodiments, a vacuum can be used to evacuate the cavities for easier filling of the cavities. The nip typically has a large enough gap such that a coherent backing is formed over the cavities. The mold surface and cavities can optionally be air or water cooled before stripping the integrally formed backing and upstanding hook elements from the mold surface such as by a stripper roll. If the posts formed upon exiting the cavities do not have loop-engaging heads, loop-engaging heads could be subsequently formed into hooks by a capping method as described in U.S. Pat. No. 5,077,870 (Melbye et al.). Typically, the capping method includes deforming the tip portions of the hook elements using heat and/or pressure. The heat and pressure, if both are used, could be applied sequentially or simultaneously.

Suitable tool rolls include those formed from a series of plates defining a plurality of post-forming cavities about its periphery such as those described, for example, in U.S. Pat. No. 4,775,310 (Fischer). Cavities may be formed in the plates by drilling or photoresist technology, for example. Other suitable tool rolls may include wire-wrapped rolls, which are disclosed along with their method of manufacturing, for example, in U.S. Pat. No. 6,190,594 (Gorman et al.). Another example of a method for forming a thermoplastic backing with upstanding posts includes using a flexible mold belt defining an array of upstanding post-shaped cavities as described in U.S. Pat. No. 7,214,334 (Jens et al.). Yet other useful methods for forming a thermoplastic backing with upstanding posts can be found in U.S. Pat. No. 6,287,665 (Hammer), U.S. Pat. No. 7,198,743 (Tuma), and U.S. Pat. No. 6,627,133 (Tuma).

The male fastening elements in the slit web or spread mechanical fastening web disclosed herein may have loop-engaging heads that have an overhang or may be upstanding posts having distal tips that can be formed into loop-engaging heads, if desired. The term "loop-engaging" as used herein relates to the ability of a male fastening element to be mechanically attached to a loop material. Generally, male fastening elements with loop-engaging heads have a head shape that is different from the shape of the post. For example, the male fastening element may be in the shape of a mushroom (e.g., with a circular or oval head enlarged with respect to the stem), a hook, a palm-tree, a nail, a T, or a J. The loop-engageability of male fastening elements may be determined and defined by using standard woven, nonwoven, or knit materials. A region of male fastening elements with loop-engaging heads generally will provide, in combination with a loop material, at least one of a higher peel strength, higher dynamic shear strength, or higher dynamic friction than a region of posts without loop-engaging heads. Male fastening elements that have "loop-engaging overhangs" or "loop-engaging heads" do not include ribs that are precursors to fastening elements (e.g., elongate ribs that are profile extruded and subsequently cut to form male fastening elements upon stretching in the direction of the ribs). Such ribs would not be able to engage loops before they are cut and stretched. Such ribs would also not be considered upstanding posts. Typically, male fastening elements that have loop-engaging heads have a maximum thickness dimension (in either dimension normal to the height) of up to about 1 (in some embodiments, 0.9, 0.8, 0.7, 0.6, 0.5, or 0.45) millimeter. In some embodiments, the male fastening elements have a maximum height (above the backing) of up to 3 mm, 1.5 mm, 1 mm, or 0.5 mm and, in some embodiments a minimum height of at least 0.05 mm, 0.1 mm, or 0.2 mm. In some embodiments, the upstanding posts have aspect ratio (that is, a ratio of height to width at the widest point) of at least about 2:1, 3:1, or 4:1.

In some embodiments of a slit web having male fastening elements useful for practicing the present disclosure, at least a portion of each loop-engaging overhang (e.g., at the cap or head) extends at a nonzero angle to the direction of the interrupted slits. In some embodiments, each male fastening element has a cap with loop engaging overhangs extending in multiple (i.e., at least two) directions. For example, the upstanding post may be in the shape of a mushroom, a nail, a palm tree, or a T. In some embodiments, the upstanding posts are provided with a mushroom head (e.g., with an oval or round cap distal from the thermoplastic backing). In other embodiments, loop-engaging overhangs (e.g., at the cap or head) on the upstanding posts of the slit web extend parallel to the MD. For example, the upstanding posts may have the shape of a J (e.g., as shown in U.S. Pat. No. 5,953,797 (Provost et al.).

In spread mechanical fastening web 10b and 10c illustrated in FIGS. 2B and 2C, the male fastening elements 12 on a first strand 26 are arranged in a series 16a that is non-parallel to a series 16b of male fastening elements 12 on a second, adjacent strand 26. The series 16a and 16b of multiple upstanding posts and the multiple strands themselves from which they project can undulate or zig-zag along the length of the spread mechanical fastening web 10b or 10c, for example, from the top edge 18 to the bottom edge 28. In the illustrated embodiment, the caps visible on the upstanding posts of the male fastening elements 12 have an oval shape, and these caps are oriented in different directions along the multiple strands 26 in the MD. When the caps are circular in shape, it may not be observed that the caps are oriented in different directions along the multiple strands 26, unless the cap is marked in some way. In the illustrated embodiment, the caps on a first strand 26 are oriented in a different direction than the caps on a second, adjacent strand 26. In embodiments in which slit web 10a includes male fastening elements having loop-engaging overhangs aligned only parallel to the MD, spreading the slit web 10a typically results in the loop-engaging overhangs oriented in different directions along the multiple strands in the MD as shown in FIG. 2C. When loop-engaging overhangs are oriented in multiple directions (e.g., not only one direction such as the machine direction), enhanced engagement of a loop material may advantageously result.

Loop materials useful for practicing some embodiments of the present disclosure (e.g., when the mechanical fastener is a loop material) can be any suitable material that interlocks with corresponding hook fastening elements. In some embodiments, the loop fastening elements are typically formed from knitted fabrics, woven fabrics, or non-woven fabrics. The term "non-woven" refers to a material having a structure of individual fibers or threads that are interlaid but not in an identifiable manner such as in a knitted fabric. Examples of non-woven webs include spunbond webs, spunlaced webs, airlaid webs, meltblown web, and bonded carded webs. The spread mechanical fastening web prepared by the method disclosed herein may include fiber loops projecting from a knitted, woven, or non-woven backing or may be extrusion-bonded, adhesive-bonded, and/or sonically-bonded fiber loops. Useful loop materials may be made of natural fibers (e.g., wood or cotton fibers), synthetic fibers (e.g., thermoplastic fibers), or a combination of natural and synthetic fibers. Examples of suitable materials for forming thermoplastic fibers include polyolefins (e.g., polyethylene, polypropylene, polybutylene, ethylene copolymers, propylene copolymers, butylene copolymers, and copolymers and blends of these polymers), polyesters, and polyamides. The fibers may also be multi-component fibers, for example, having a core of one thermoplastic material and a sheath of another thermoplastic material.

In some embodiments, the loop material comprises a fibrous layer disposed on a backing. Suitable backings include textiles, paper, thermoplastic films (e.g., single- or multilayered films, coextruded films, laterally laminated films, or films comprising foam layers), and combinations thereof. For thermoplastic backings, the thermoplastic can be any of those described above in connection with a thermoplastic backing having male fastening elements. Examples of suitable loop materials are described, for example, in U.S. Pat. No. 5,256,231 (Gorman et al.) and U.S. Pat. No. 5,389,416 (Mody et al.). As described in U.S. Pat. No. 5,256,231 (Gorman et al.), the fibrous layer in a loop material according to some embodiments disclosed herein comprises arcuate portions projecting in the same direction from spaced anchor portions on the backing.

In embodiments wherein the mechanical fastening web either has male fastening elements (e.g., upstanding posts) or a fibrous layer on a backing, the thickness of the backing may be up to about 400, 250, 150, 100, 75 or 50 micrometers, depending on the desired application. In some embodiments, the thickness of the backing is in a range from 30 to about 225 micrometers, from about 50 to about 200 micrometers, or from about 100 to about 150 micrometers. In some embodiments wherein the backing is a thermoplastic backing, the thermoplastic backing has stretch-induced molecular orientation, for example, when the thermoplastic backing is stretched after formation of upstanding posts. In other embodiments, the thermoplastic backing or the spread mechanical fastening web is not provided with macroscopic stretch-induced molecular orientation in the direction of the interrupted slits or in the direction of spreading. In these embodiments, there may be some stress-induced orientation localized in the bridging regions.

Figure 5:
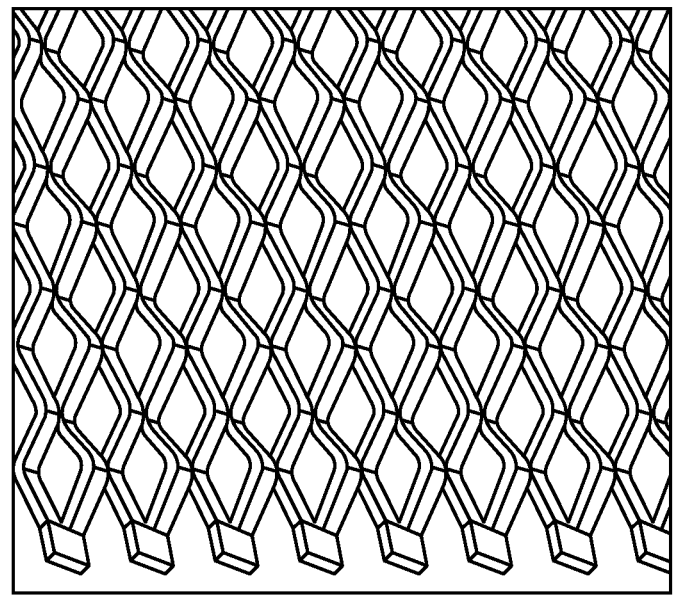
FIG. 5 is an illustration of the twisting of strands of a slit web portion when it is spread apart.

The method of the present disclosure can typically spread a slit mechanical fastening web while advantageously not allowing all of the multiple strands of the spread mechanical fastening web to twist out-of-plane. Twisting out-of-plane can result when spreading a slit web as shown in FIG. 5. Pieces of loop material were attached to the edges of a slit mechanical fastener web portion with male fastening elements such as that shown in FIG. 2A. When the pieces of loop material were pulled apart, the individual strands of the slit web tended to twist out of the plane of the web as shown in FIG. 5. The amount of out-of-plane twisting is typically affected, for example, by the extent to which the slit backing is spread. Twisted strands of the spread mechanical fastening web create a non-uniform contact surface, which can complicate heat transfer to the web and complicate the use of a nip in further web processing (e.g., annealing or laminating as described below) since the twisted strands may be crushed by the nip.

A number of features of the method and apparatus according to the present disclosure can help control the tendency of the strands of the slit web to twist out-of-plane. The tension applied in the machine direction that causes the crowned surface to exert a force on the slit web normal to the slit web can help to keep the multiple strands in plane. Also, the geometry of the crown may be designed to limit the degree of spreading such that the strands are less likely to twist out-of-plane. In this way, the method disclosed herein may be considered to maintain or constrain at least some of the multiple strands in an arrangement substantially coplanar with the plane of the web, for example, as the web leaves the crowned surface. A substantially "coplanar" arrangement refers to the strands occupying substantially the same plane. The term "substantially" in this regard can mean that at least some of the multiple strands can be twisted out of plane by up to 15, 10, or 5 degrees. The phrase "at least some" with regard to the multiple strands being constrained refers to at least 25, 50, 75, or 90 percent or more of the multiple strands being constrained.

A number of web handling or web processing techniques may be useful in a variety of combinations for some embodiments of the method disclosed herein. For any of the aforementioned embodiments of the method according to the present disclosure, providing a slit web having upstanding posts or loops with interrupted slits can be carried out in a variety of ways. For example, rotary die cutting of a continuous web having male fastening elements or loops as described above may be useful. Interrupted slits can be made, for example, by using rotary cutting blades having gaps to form the bridging regions. The height of the blade in the gaps may be adjusted to allow for the bridging regions to be partially cut or not cut at all, depending on the desired embodiment. Other cutting methods (e.g., laser cutting) may also be useful. Cutting can be performed from either surface of the continuous web. A slit may be cut "through" the web having mechanical fastening elements, which means that the slit cuts through the entire thickness of the web. In other embodiments, the slit may be a partial-depth slit as long as the spreading device can pull apart the partial depth slit. The partial-depth slit may penetrate, for example, 80, 85, or 90 percent of the thickness of the web or more, which means the solution to the equation:

$$(\text{depth of the slit divided by the thickness of the web}) \times 100$$

is at least 80, 85, or 90 in some embodiments. Other methods of slitting a web can be found, for example, in U.S. Pat. Appl. Pub. No. 2011/0313389 (Wood et al.).

When male fastening elements are formed as described above, for example, where a thermoplastic material is fed onto a continuously moving mold surface with cavities having the inverse shape of upstanding posts, slitting the web and spreading the slit web according to the method disclosed herein can be carried out before or after a capping step is carried out to form loop-engaging heads. Also, deforming the distal tip to form a cap can be carried out, for example, after slitting through the web but before spreading the slit web; after spreading the slit web but before annealing (described below); or after annealing as desired. The formation of male fastening elements can also include a step in which the shape of the cap is changed, for example, as described in U.S. Pat. No. 6,132,660 (Kampfer). Such a cap modifying step can be carried out directly after capping or after any of the slitting, spreading, or further processing steps described herein.

In some embodiments, the method according to the present disclosure further comprises heating the spread mechanical fastening web. In some embodiments, the method according to the present disclosure further comprises annealing the spread mechanical fastening web. In some embodiments, annealing comprises heating the spread mechanical fastening web. In some embodiments, annealing comprises heating and then cooling (e.g., rapidly cooling) the spread mechanical fastening web to maintain its configuration. Heating and/or annealing can be carried out, for example, after the spread mechanical fastening web has been spread to the final desired extent or at an intermediate stage, for example, if the spread mechanical fastening web is spread a second time with a second crowned surface. Annealing can be useful, for example, depending on the extent of spreading, and can be useful to maintain the openings between multiple strands, for example, when the width of the slit web has been increased by at least 50 percent. Annealing can also be useful, for example, for maintaining at least some of the multiple strands in a substantially coplanar arrangement. In some embodiments, heating is only applied to the second surface of the spread mechanical fastening web (i.e., the surface opposite the first surface from which the mechanical fastening elements project) to minimize any damage to the mechanical fastening elements that may result from heating. Heating may be carried out on a continuous web, for example, using heated rollers, or using non-contact heating methods such as IR irradiation, hot air treatment, or by directing the web through a heated chamber.

Figure 6:
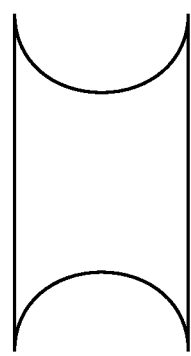
FIG. 6 is a schematic illustration of a roller having an inverse geometry to the crown surface useful for some embodiments of the method according to the present disclosure.

In some embodiments, the method of making a mechanical fastener disclosed herein further includes moving the slit web over a high-friction roller before moving the slit web over the crowned surface, wherein the high-friction roller has a surface that has the inverse geometry of the crowned surface. A schematic illustration of the shape of an embodiment of this high-friction roller is shown in FIG. 6. The high-friction roller with the inverse geometry of the crowned surface may help to decrease tension concentration in the spread mechanical fastening web. When the slit web is moved over a crowned surface, a concentration of tension can be created along the lines of longest path length for a web, which, for some embodiments, is in the center of the web. The high friction roller with the inverse geometry of the crowned surface would pretension the side edges of the slit web, which would lead to more uniform tension in the web after the slit web is moved over the crowned surface. To pretension the slit web, high frictional forces may be desirable to prevent cross-directional movement. Therefore, a high-friction roller may be useful.

Figure 7:
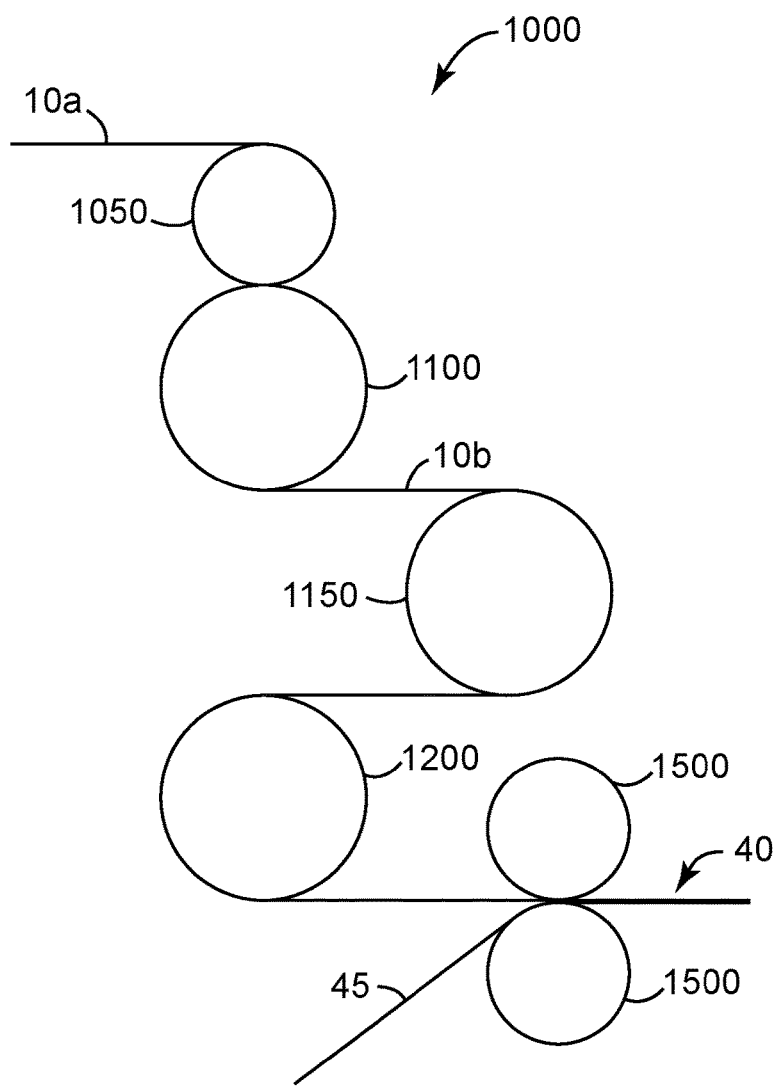
FIG. 7 is a diagrammatical view of an embodiment of carrying out the method of making a mechanical fastener disclosed herein.

A diagrammatical representation of an embodiment of an apparatus 1000 for carrying out the method of the present disclosure is shown in FIG. 7. In FIG. 7, slit web 10a is directed over roller 1050, which may be useful, for example, for adjusting the tension in the web 10a. Slit web 10a is then spread by moving it over crowned surface 1100 to provide spread mechanical fastening web 10b. Spread mechanical fastening web 10b can optionally be handled by one or more other rollers 1150, which may be a rotating heated cylinder (or heated roller) as described above. In some embodiments, roller 1150 may be a high-friction roller (e.g., comprising a rubbery material or a material with a rough surface). The high-friction roller may be heated or chilled, if desired, or may be useful at room temperature. A high-friction roller may be useful, for example, for holding the spread mechanical fastening web in a spread configuration whether or not the web is annealed. In the illustrated embodiment, the spread mechanical fastening web 10b is then moved over a second crowned surface 1200 where the web can be spread to a greater extent. In the illustrated embodiment, the spread mechanical fastening web is then laminated to a carrier web 45 to form a laminate 40. Lamination is carried out in a nip formed by rollers 1500. In some embodiments, before lamination, spread mechanical fastening web can be directed onto a rotating heated cylinder optionally followed by a rotating chilled cylinder to anneal and rapidly cool the spread mechanical fastening web.

Various web handling and design techniques may be useful for decreasing the tendency of the slide web to slide off of the crowned surface, for example, if the cross-directional force in one direction becomes greater for some reason than the cross direction force in the opposite direction as described above. In addition to the guiding mechanisms described above, minimizing the size of the crowned surface to get the desired amount of spreading of the slit web may be desirable. Also positioning upstream and downstream rollers 1050 and 1150 close to the crowned surface 1100 may be useful as well as positioning the rollers such that the slit web bends over or wraps around a minimal portion of the crowned surface. Each of these may be useful alone or in combination.

For any of the embodiments of the method of making a mechanical fastener disclosed herein, the spread mechanical fastening web may be in the form of a roll. The bridging regions interrupting the interrupted slits allow the spread mechanical fastening web to be handled as an integral unit, for example, to be handled in roll form and converted as desired. Although the bridging regions in the spread mechanical fastening web allow it to be handled as an integral unit, it may be useful to laminate the spread mechanical fastening web to a carrier (e.g., even a sacrificial carrier) for ease of handling, for fixing the multiple strands of the spread mechanical fastening web in a spread configuration to maintain the separation between the multiple strands, or for making a fastening laminate for a selected application. The spread mechanical fastening web may be joined to a carrier, for example, by lamination (e.g., extrusion lamination), adhesives (e.g., pressure sensitive adhesives), or other bonding methods (e.g., ultrasonic bonding, compression bonding, or surface bonding).

The carrier 45 may be continuous (i.e., without any through-penetrating holes) or discontinuous (e.g. comprising through-penetrating perforations or pores). The carrier may comprise a variety of suitable materials including woven webs, non-woven webs (e.g., spunbond webs, spunlaced webs, airlaid webs, meltblown web, and bonded carded webs), textiles, plastic films (e.g., single- or multi-layered films, coextruded films, laterally laminated films, or films comprising foam layers), and combinations thereof. In some embodiments, the carrier is a fibrous material (e.g., a woven, nonwoven, or knit material). In some embodiments, the carrier comprises multiple layers of nonwoven materials with, for example, at least one layer of a meltblown nonwoven and at least one layer of a spunbonded nonwoven, or any other suitable combination of nonwoven materials. For example, the carrier may be a spunbond-meltbond-spunbond, spunbond-spunbond, or spunbond-spunbond-spunbond multilayer material. Or, the carrier may be a composite web comprising a nonwoven layer and a dense film layer. Fibrous materials that may provide useful carriers may be made from any of the fibers described above as useful for making loop materials. Useful carriers may have any suitable basis weight or thickness that is desired for a particular application. For a fibrous carrier, the basis weight may range, e.g., from at least about 5, 8, 10, 20, 30, or 40 grams per square meter, up to about 400, 200, or 100 grams per square meter. The carrier may be up to about 5 mm, about 2 mm, or about 1 mm in thickness and/or at least about 0.1, about 0.2, or about 0.5 mm in thickness.

In some embodiments where the spread mechanical fastening web includes a thermoplastic backing (e.g., with upstanding posts or a fibrous layer thereon) the thermoplastic backing can be joined to a fibrous web carrier using surface bonding or loft-retaining bonding techniques. The term "surface-bonded" when referring to the bonding of fibrous materials means that parts of fiber surfaces of at least portions of fibers are melt-bonded to the second surface of the backing, in such a manner as to substantially preserve the original (pre-bonded) shape of the second surface of the backing, and to substantially preserve at least some portions of the second surface of the backing in an exposed condition, in the surface-bonded area. Quantitatively, surface-bonded fibers may be distinguished from embedded fibers in that at least about 65% of the surface area of the surface-bonded fiber is visible above the second surface of the backing in the bonded portion of the fiber. Inspection from more than one angle may be necessary to visualize the entirety of the surface area of the fiber. The term "loft-retaining bond" when referring to the bonding of fibrous materials means a bonded fibrous material comprises a loft that is at least 80% of the loft exhibited by the material prior to, or in the absence of, the bonding process. The loft of a fibrous material as used herein is the ratio of the total volume occupied by the web (including fibers as well as interstitial spaces of the material that are not occupied by fibers) to the volume occupied by the material of the fibers alone. If only a portion of a fibrous web has the second surface of the backing bonded thereto, the retained loft can be easily ascertained by comparing the loft of the fibrous web in the bonded area to that of the web in an unbonded area. It may be convenient in some circumstances to compare the loft of the bonded web to that of a sample of the same web before being bonded, for example, if the entirety of fibrous web has the second surface of the backing bonded thereto. In some of these embodiments, the joining comprises impinging heated gaseous fluid (e.g., ambient air, dehumidified air, nitrogen, an inert gas, or other gas mixture) onto a first surface of the fibrous web carrier while it is moving; impinging heated fluid onto the second surface of the backing while the continuous web is moving, wherein the second surface is opposite the fibrous layer, loop, or upstanding posts the backing; and contacting the first surface of the fibrous web with the second surface of the backing so that the first surface of the fibrous web is melt-bonded (e.g., surface-bonded or bonded with a loft-retaining bond) to the second surface of the backing. Impinging heated gaseous fluid onto the first surface of the fibrous web and impinging heated gaseous fluid on the second surface of the backing may be carried out sequentially or simultaneously. Further methods and apparatus for joining a continuous web to a fibrous carrier web using heated gaseous fluid may be found in U.S. Pat. Appl. Pub. Nos. 2011/0151171 (Biegler et al.) and 2011/0147475 (Biegler et al.).

In some embodiments wherein the spread mechanical fastening web is joined to a carrier, one or more zones of the carrier may comprise one or more elastically extensible materials extending in at least one direction when a force is applied and returning to approximately their original dimension after the force is removed. However, in some embodiments, at least the portion of the carrier joined to the multiple strands of the backing or loop material is not stretchable. In some embodiments, the portion of carrier joined to the multiple strands will have up to a 10 (in some embodiments, up to 9, 8, 7, 6, or 5) percent elongation in the CD. In some embodiments, the carrier may be extensible but nonelastic. In other words, the carrier may have an elongation of at least 5, 10, 15, 20, 25, 30, 40, or 50 percent but substantially no recovery from the elongation (e.g., up to 10 or 5 percent recovery). Suitable extensible carriers may include nonwovens (e.g., spunbond, spunbond meltblown spunbond, or carded nonwovens). In some embodiments, the nonwoven may be a high elongation carded nonwoven (e.g., HEC). In some embodiments, the carrier is not pleated.

In some embodiments wherein the spread mechanical fastening web is joined to a carrier, the carrier is provided with a layer of adhesive. In some of these embodiments, the spread mechanical fastening web is bonded to the carrier with the adhesive to form a laminate, and the adhesive is exposed between the multiple strands in the laminate.

In some embodiments, the method according to the present disclosure includes cutting the spread mechanical fastening web in the CD to provide a spread mechanical fastening patch. Such cutting can be carried out, for example, after the spread mechanical fastening web is laminated to a carrier, and the patch can be considered a fastening laminate.

The fastening laminates made by the methods disclosed herein are useful, for example, in absorbent articles. Absorbent articles may have at least a front waist region, a rear waist region, and a longitudinal center line bisecting the front waist region and the rear waist region, wherein at least one of the front waist region or the rear waist region comprises the fastening laminate disclosed herein. The fastening laminate may be in the form of a fastening tab or landing zone that is bonded to at least one of the front waist region or the rear waist region. A fastening tab may extend outwardly from at least one of the left longitudinal edge or the right longitudinal edge of the absorbent article. In other embodiments, the fastening laminate may be an integral ear portion of the absorbent article. The carrier at the user's end of a fastening tab may exceed the extension of the spread mechanical fastening patch thereby providing a fingerlift. When the spread mechanical fastening patch is used in a fastening tab, exposed adhesive that may be present in some embodiments between the multiple strands of the spread mechanical fastening patch may be useful for "anti-flagging" or for maintaining the disposable absorbent article in a rolled up state after use. Also when the spread mechanical fastening patch is used as a landing zone or fastening tab, exposed adhesive that may be present in some embodiments between the multiple strands of the spread mechanical fastening patch may be useful to provide a combination of mechanical and adhesive fastening. The fastening laminate made by the methods disclosed herein may also be useful, for example, for disposable articles such as sanitary napkins.

The mechanical fasteners and laminates made according to the present disclosure may also be useful in many other fastening applications, for example, assembly of automotive parts or any other application in which releasable attachment may be desirable.

Some Embodiments of the Disclosure

In a first embodiment, the present disclosure provides a method of making a mechanical fastener, the method comprising:

providing a slit web having mechanical fastening elements and a length in a machine direction, wherein the slit web includes a plurality of laterally separated interrupted slits that are interrupted by intact bridging regions of the web, wherein the interrupted slits extend in a first direction that is non-parallel to a cross-machine direction, and wherein for at least some adjacent interrupted slits, the intact bridging regions are staggered in a direction transverse to the first direction;

applying tension to the slit web in the machine direction; and spreading the slit web in a cross-machine direction by moving the slit web over a crowned surface to provide a spread mechanical fastening web, wherein the spread mechanical fastening web comprises multiple strands of the slit web attached to each other at least at some of the intact bridging regions and separated from each other between at least some of the intact bridging regions, and wherein at least a portion of the crowned surface is an air bearing; or at least a portion of the crowned surface is a low-friction surface, and the crowned surface and the slit web are not moving at the same speed in the same direction.

In a second embodiment, the present disclosure provides the method of the first embodiment, wherein the crowned surface does not rotate.

In a third embodiment, the present disclosure the method of the first or second embodiment, wherein the crowned surface is an air bearing.

In a fourth embodiment, the present disclosure provides the method of the first or second embodiment, wherein at least a portion of the crowned surface is a low-friction surface, and the crowned surface and the slit web are not moving at the same speed in the same direction.

In the fifth embodiment, the present disclosure provides the method of the fourth embodiment, wherein the low-friction, crowned surface is made from a smooth or polished metal or a smooth plastic.

In a sixth embodiment, the present disclosure provides the method of the fourth embodiment, wherein the crowned surface has a low-friction coating.

In a seventh embodiment, the present disclosure provides the method of any one of the first to sixth embodiments, wherein the crowned surface is provided with at least one ridge.

In an eighth embodiment, the present disclosure provides the method of the seventh embodiment, wherein the at least one ridge is at the apex of the crowned surface.

In a ninth embodiment, the present disclosure provides the method of the seventh or eighth embodiment, wherein the mechanical fastening elements are male fastening elements, wherein the slit web is arranged so that the male fastening elements face toward the crowned surface, and wherein the at least one ridge is a guiding ridge that fits between the male fastening elements.

In a tenth embodiment, the present disclosure provides the method of the seventh or eighth embodiment, wherein the crowned surface is provided with at least two guiding ridges, wherein the slit web has at least one continuous rib centered on a surface opposite to a surface having the mechanical fastening elements, wherein the slit web is arranged so that the continuous rib faces toward the crowned surface, and wherein the continuous rib fits between the two guiding ridges on the crowned surface.

In an eleventh embodiment, the present disclosure provides the method of any one of the first to tenth embodiments, wherein the crowned surface has a curvature that varies such that the curvature of the crowned surface at a point where the crowned surface first contacts the slit web is less than the curvature at a point where the crowned surface last contacts the spread mechanical fastening web.

In a twelfth embodiment, the present disclosure provides the method of any one of the first to eleventh embodiments, further comprising moving the slit web over a high-friction roller before moving the slit web over the crowned surface, wherein the high-friction roller has a surface that has an inverse geometry of the crowned surface.

In a thirteenth embodiment, the present disclosure provides the method of any one of the first to twelfth embodiments, further comprising heating the spread mechanical fastening web, for example, to anneal the spread mechanical fastening web.

In a fourteenth embodiment, the present disclosure provides the method of the thirteenth embodiment, wherein heating comprises directing the spread mechanical fastening web onto a rotating heated cylinder.

In a fifteenth embodiment, the present disclosure provides the method of the thirteenth embodiment, wherein heating comprises using non-contact heating.

In a sixteenth embodiment, the present disclosure provides the method of any one of the first to fifteenth embodiments, further comprising directing the spread mechanical fastening web onto a high-friction roller.

In a seventeenth embodiment, the present disclosure provides the method of the sixteenth embodiment, wherein the high-friction roller is heated.

In an eighteenth embodiment, the present disclosure provides the method of the sixteenth embodiment, wherein the high-friction roller is chilled.

In a nineteenth embodiment, the present disclosure provides the method of any one of the first to eighteenth embodiments, further comprising directing the spread mechanical fastening web onto a rotating chilled cylinder.

In a twentieth embodiment, the present disclosure provides the method of any one of the first to nineteenth embodiments, wherein the slit web is spread such that the width of the spread mechanical fastening web is up to 100 percent greater than the width of the slit web.

In a twenty-first embodiment, the present disclosure provides the method of any one of the first to twentieth embodiments, further comprising spreading the spread mechanical fastening web in a cross-machine direction a second time by moving the slit web over a second crowned surface.

In a twenty-second embodiment, the present disclosure provides the method of the twenty-first embodiment, wherein the second crowned surface and the spread mechanical fastening web are not moving at the same speed in the same direction, and wherein at least a portion of the second crowned surface is a low-friction surface.

In a twenty-third embodiment, the present disclosure provides the method of the twenty-first or the twenty-second embodiments, wherein the second crowned surface is an air bearing.

In a twenty-fourth embodiment, the present disclosure provides the method of any one of the twenty-first to twenty-third embodiments, wherein the second crowned surface is provided with at least one ridge.

In a twenty-fifth embodiment, the present disclosure provides the method of any one of the twenty-first to twenty-fourth embodiments, wherein the spread mechanical fastening web is spread a second time such that its width is up to 200 percent greater than the width of the slit web.

In a twenty-sixth embodiment, the present disclosure provides the method of any one of the first to twenty-fifth embodiments, wherein the first direction is the machine direction.

In a twenty-seventh embodiment, the present disclosure provides the method of any one of the first to twenty-sixth embodiments, further comprising laminating the spread mechanical fastening web to a carrier.

In a twenty-eighth embodiment, the present disclosure provides the method of the twenty-seventh embodiment wherein the carrier is a nonwoven web.

In a twenty-ninth embodiment, the present disclosure provides the method of the twenty-seventh or twenty-eighth embodiments, wherein the carrier is provided with a layer of an adhesive.

In a thirtieth embodiment, the present disclosure provides the method of the twenty-ninth embodiment, wherein the spread mechanical fastening web is bonded to the carrier with the adhesive to form a laminate, and wherein the adhesive is exposed between the multiple strands in the laminate.

In a thirty-first embodiment, the present disclosure provides the method of any one of the first to thirtieth embodiments, wherein there is no macroscopic stretch-induced molecular orientation in the slit backing in the cross-direction.

In a thirty-second embodiment, the present disclosure provides the method of any one of the first to thirty-first embodiments, wherein the multiple strands of the slit web attached to each other at least at some of the intact bridging regions form an angle of less than 90 degrees.

In a thirty-third embodiment, the present disclosure provides the method of any one of the first to thirty-second embodiments, wherein the mechanical fastening elements are male fastening elements comprising upstanding posts having bases attached to the slit web. The male fastening elements may also comprise caps distal from the slit web.

In a thirty-fourth embodiment, the present disclosure provides the method of the thirty-third embodiment, wherein the width dimension of each of the multiple strands is wider than at least the bases of the upstanding posts.

In a thirty-fifth embodiment, the present disclosure provides the method of the thirty-third or thirty-fourth embodiment, wherein the caps have loop-engaging overhangs extending beyond the upstanding posts at a non-zero angle to the direction of the interrupted slits.

In a thirty-sixth embodiment, the present disclosure provides the method of any one of the thirty-third to thirty-fifth embodiments, further comprising providing a thermoplastic backing having multiple rows of the upstanding posts, wherein providing the slit web comprises slitting through the thermoplastic backing between at least some pairs of adjacent rows of the upstanding posts.

In a thirty-seventh embodiment, the present disclosure provides the method of any one of the first to thirty-second embodiments, wherein the slit web has loops.

This disclosure is not limited to the above-described embodiments but is to be controlled by the limitations set forth in the following claims and any equivalents thereof. This disclosure may be suitably practiced in the absence of any element not specifically disclosed herein.

What is claimed is:

1. A method of making a mechanical fastener, the method comprising:
   providing a slit web having mechanical fastening elements and a length in a machine direction, wherein the slit web includes a plurality of laterally separated interrupted slits that are interrupted by intact bridging regions of the web, wherein the interrupted slits extend in a first direction that is non-parallel to a cross-machine direction, and wherein for at least some adjacent interrupted slits, the intact bridging regions are staggered in a direction transverse to the first direction;
   applying tension to the slit web in the machine direction; and
   spreading the slit web in a cross-machine direction by moving the slit web over a crowned surface to provide a spread mechanical fastening web, wherein the spread mechanical fastening web comprises multiple strands of the slit web attached to each other at least at some of the intact bridging regions and separated from each other between at least some of the intact bridging regions, and wherein
   at least a portion of the crowned surface is an air bearing; or
   at least a portion of the crowned surface is a low-friction surface, and the crowned surface and the slit web are not moving at the same speed in the same direction.

2. The method of claim 1, wherein the crowned surface does not rotate.

3. The method of claim 1, wherein at least a portion of the crowned surface is a low-friction surface, and wherein the low-friction, crowned surface is made from a smooth or polished metal or a smooth plastic.

4. The method of claim 1, wherein at least a portion of the crowned surface is a low-friction surface, and wherein the crowned surface has a low-friction coating.

5. The method of claim 1, wherein the crowned surface is provided with at least one ridge at its apex.

6. The method of claim 5, wherein the mechanical fastening elements are male fastening elements, wherein the slit web is arranged so that the male fastening elements face toward the crowned surface, and wherein the at least one ridge is a guiding ridge that fits between the male fastening elements.

7. The method of claim 1, wherein the crowned surface has a curvature that varies such that the curvature of the crowned surface at a point where the crowned surface first contacts the slit web is less than the curvature at a point where the crowned surface last contacts the spread mechanical fastening web.

8. The method of claim 1, further comprising moving the slit web over a high-friction roller before moving the slit web over the crowned surface, wherein the high-friction roller has a surface that has an inverse geometry of the crowned surface.

9. The method of claim 1, further comprising heating the spread mechanical fastening web.

10. The method of claim 9, wherein heating comprises directing the spread mechanical fastening web onto a rotating heated cylinder.

11. The method of claim 1, further comprising directing the spread mechanical fastening web onto a high-friction roller.

12. The method of claim 1, wherein the multiple strands of the slit web attached to each other at least at some of the intact bridging regions form an angle of less than 90 degrees.

13. The method of claim 1 further comprising spreading the spread mechanical fastening web in a cross-machine direction a second time by moving the slit web over a second crowned surface.

14. The method of claim 1, further comprising laminating the spread mechanical fastening web to a carrier.

15. The method of claim 14, wherein the carrier is provided with a layer of adhesive, wherein the spread mechanical fastening web is bonded to the carrier with the adhesive to form a laminate, and wherein the adhesive is exposed between the multiple strands in the laminate.

16. The method of claim 14, wherein the carrier is a nonwoven web.

17. The method of claim 9, wherein heating the spread mechanical fastening web comprises using non-contact heating.

18. The method of claim 1, wherein the first direction is the machine direction.

19. The method of claim 1, wherein the mechanical fastening elements are male fastening elements comprising upstanding posts having bases attached to the slit web.

20. The method of claim 1, wherein the slit web has loops.

* * * * *